United States Patent
Sterphone et al.

(12)

(10) Patent No.: US 6,503,515 B1
(45) Date of Patent: Jan. 7, 2003

(54) COSMETIC COMPOSITION COMPRISING FARNESOL, FARNESYL ACETATE AND PANTHENYL TRIACETATE

(75) Inventors: Stacy Sterphone, Somerville, NJ (US); Elisa Burdzy, Milford, NJ (US)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/283,146

(22) Filed: Apr. 1, 1999

(51) Int. Cl.[7] .............................. A61K 6/00; A61K 7/00

(52) U.S. Cl. ........................ 424/401; 424/400; 424/489

(58) Field of Search .................................. 424/400, 401, 424/489, 43, 46; 514/844

*Primary Examiner*—Dameron L. Jones
(74) *Attorney, Agent, or Firm*—Finnegan, Henderson, Farabow, Garrett & Dunner, L.L.P.

(57) ABSTRACT

A cosmetic composition comprising panthenyl triacetate, farnesyl acetate and farnesol. Preferably, the composition includes the farnesol, farnesyl acetate and panthenyl triacetate in an amount effective for enhancing the texture of the composition relative to similar compositions lacking these ingredients.

67 Claims, 3 Drawing Sheets

COSMETIC COMPOSITION COMPRISING FARNESOL, FARNESYL ACETATE AND PANTHENYL TRIACETATE

The present invention relates to a cosmetic composition comprising farnesol, farnesyl acetate and panthenyl triacetate, particularly in an amount effective for enhancing the texture of the composition. In particular, the present invention relates to powder compositions that can have a silky feel and are useful as face powders, blushes, eyeshadows and the like.

The cosmetic industry is continually researching cosmetic compositions that are easier, more efficient or less expensive to manufacture yet also provide the user beneficial characteristics such as enhanced texture, spreadability, moisturization, sebum-regulation and consistency. Cosmetic powder formulations such as blushes, face powders and eyeshadows, are formulated with a liquid component that aids in, for example, compaction, pigment-wetting, and skin-adhesion. However, liquid ingredients of powder compositions can have a deleterious effect on the textural attributes of the finished product. Therefore, conventional formulations can accept a maximum level of liquid, after which the texture can be negatively impacted, becoming heavy and waxy-feeling, and performing poorly if presented in a compacted form.

Cosmetic compositions of the present invention comprise farnesol, farnesyl acetate and panthenyl triacetate and preferably a powder. Inclusion of these liquid ingredients can surprisingly and unexpectedly provide a light, silky texture. In particular, the powder compositions of the present invention can provide a "suede"-like feel and can avoid being heavy or oily as would be expected with compositions containing comparable levels of liquids. The powder compositions can also be natural looking and can avoid being dry, powdery or cakey looking when applied to the skin.

The compositions of the present invention can also be surprisingly easier to compact than prior art formulations while at the same time enhancing the integrity and consistency of the composition. In particular, the compositions of the present invention can provide consistent cakes which maintain their integrity when pressed at a wider range of pressures. For example, the compositions can perform well in ship tests and can retain their unity when provided in compacts, even when used down to the bottom of the compact.

Accordingly, it is an object of the present invention to provide cosmetic powder compositions that comprise liquid ingredients for imparting beneficial characteristics such as sebum-regulation and enhanced texture without causing a heavy, waxy feel.

It is a further object of the present invention to provide cosmetic compositions that include liquids yet are easy to compact and do not have poor performance when compacted.

The above and other objects, advantages and features of the invention will be more readily understood from the following detailed description of preferred embodiments of the invention.

Figure 1:
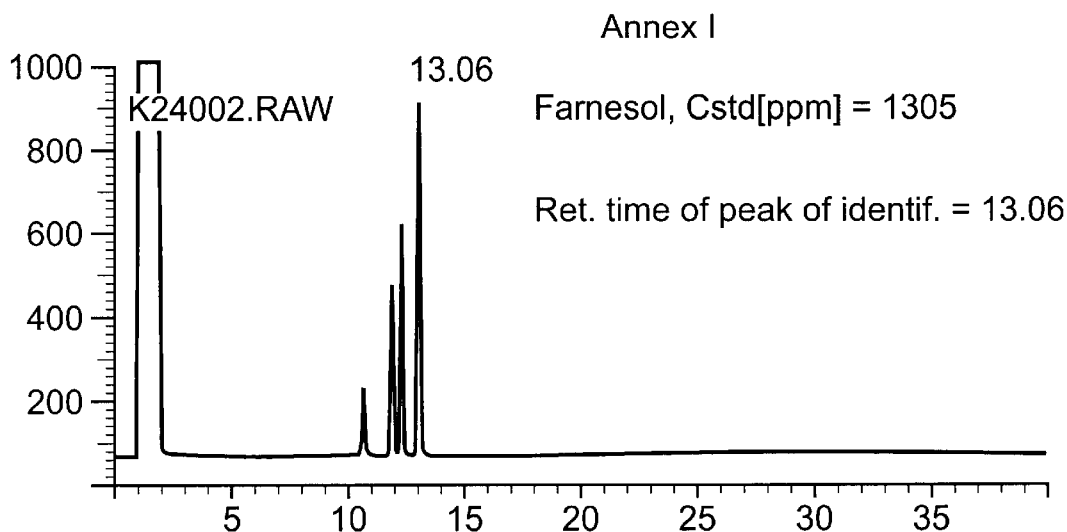
FIG. 1 is a chromatogram of a sample of farnesol.

The cosmetic composition of the present invention contains farnesol, farnesyl acetate and panthenyl triacetate. Preferably, the compositions of the present invention also include a powder and/or a compatible liquid binder system.

The powder is preferably talc but can be any powder, or mixture thereof, suitable for cosmetic compositions. Such powders are defined in the International Cosmetic Ingredient Dictionary and Handbook, 7$^{th}$ Edition, The Cosmetic, Toiletry and Fragrance Association, Washington, D.C. (1997). These publications are specifically incorporated by reference herein.

The powder is present in the compositions, whether they are loose or pressed, in an amount preferably ranging from 2% to 98%, more preferably 3% to 97% by weight of the composition. More preferably, the powder is included in an amount ranging from 34% to 97%, even more preferably 35% to 96% by weight of the total composition.

The liquid binder system can contain, for example, one or more of tridecyl neopentanoate, octyl palmitate, isocetyl stearoyl stearate, octyldodecyl stearoyl stearate, laureth-2-actanoate, dimethylolpropane tetraisostearate, isocetyl stearyl stearate, diisostearyl malate, triisostearyl citrate, trimethylpropane triisostearate, dimethicone, cetyl dimethicone, dimethiconol, triisooctyl citrate, trimethylsiloxysilicate, cyclopentasiloxane, triisostearyl citrate, isostearyl neopentanoate or any of the liquid binders listed in the International Cosmetic Ingredient Dictionary and Handbook.

As discussed above in connection with the powder constituent, the liquid binder, as well as any constituents mentioned hereinafter, encompass classes of materials within the meaning of those ingredients as defined in the aforementioned International Cosmetic Ingredient Dictionary and Handbook, 7$^{th}$ Edition.

If the powder composition is a pressed powder, the powder composition comprises liquid binder preferably in an amount ranging from 1% to 11%, more preferably 2% to 10% by weight of the total composition. If the powder composition is a loose powder, the powder composition comprises liquid binder preferably in an amount ranging from 0.4% to 4%, more preferably 0.5% to 3% by weight. Preferably, the liquid binder is a liquid binder system comprising a mixture of liquid binders and, for pressed powder compositions, the liquid binder system is included in the composition preferably in an amount ranging from 1% to 7%, more preferably 2% to 6% by weight of the total composition.

The farnesol, farnesyl acetate and panthenyl triacetate may preferably be provided as a blend or else they may be added individually into the composition. The farnesol, farnesyl acetate and panthenyl triacetate are provided into the mixture preferably in an amount effective for enhancing the texture of the composition relative to similar compositions lacking these ingredients and in an amount effective for improving the texture of the composition relative to the Estee Lauder Double Matte Pressed Powder product, described below in comparative Example 30.

If the three components are introduced into the composition as a blend, the "effective amount" would preferably be inclusion of each ingredient an amount of from 15% to 65%, more preferably 25% to 50% by weight of the blend. Preferably, the liquid blend is "Unitrienol T-27" available from Induchem AG located at Lagerstrasse 14, CH-8600 Dubendorf 1, Switzerland.

If the three components are separately added to the mixture, the total amount of each of the components in the composition is preferably the same as though they were added as a blend.

If the powder composition is a pressed or a loose powder, the liquid blend can be present in the composition in amounts preferably ranging from down to 0.20%, more preferably down to 0.25%. A person of skill in the art will be able to recognize the highest amount of liquid blend that can be added to the powder composition based on, for example for pressed powders, compaction issues such as difficulty of pressing the composition. Similarly, a person of skill in the art will recognize that the liquid blend can be included in greater amounts in loose powder compositions as compared to pressed powder compositions. For pressed powders, the liquid blend can preferably be included in amounts ranging from 0.20% to 9%, more preferably from 0.25% to 8%. More preferably, the liquid blend is included in the pressed powder composition in an amount ranging from 0.5% to 6%, even more preferably 1.0% to 5% by weight of the total composition.

The powder compositions of the present invention can optionally include other common cosmetic ingredients such as, but not limited to, dry binders or compaction aids, pigment wetters, absorbents, preservatives, fillers or bulking agents, texturizers in addition to the liquid blend, emollients, film formers, pigments or colorants, fragrances, sebum displacers, optical diffusers, components useful for enhancing skin adhesion, spreadablity, oil absorption and lightening of texture, as well as astringents, thickeners and active ingredients such as sunscreens. Again, most of these additives and others are defined and exemplified in the International Cosmetic Ingredient Dictionary and Handbook, 7$^{th}$ Edition, which has been specifically incorporated by reference herein. A person of ordinary skill in the art should recognize when it would be appropriate to use these ingredients and in what amounts they should be used depending upon the features of the cosmetic composition into which the farnesol, panthenyl triacetate and farnesyl acetate are incorporated. For example, the amount of pigment can vary depending upon the complexion intended to be matched and could be up to 90% by weight of the total composition. In other applications, the amount of pigment would more appropriately be 20% by weight of the total composition or even absent from the composition.

Preferred optional ingredients include: fillers, pigments, dry binders, absorbents, such as oil absorbents, astringents, sebum displacers, preservatives, anti-caking agents and texturizers. Non-limiting examples of these ingredients include the following. Suitable fillers can be micas or aluminosilicates, clays, kaolin or aluminum silicate hydrates, boron nitrides and talcs or magnesium silicate hydrates and starches. Examples of pigments which can be used include carmine, ultramarine and lolustre pigment with barium sulfate which is a mixture of mica, titanium dioxide and. barium sulfate, as well as zinc and iron oxides such as zinc oxide 66, cosmetic grade yellow iron oxide BC-7055, cosmetic grade red iron oxide BC-7051, cosmetic grade black iron oxide BC-7053 and Sicomet Brun ZP 3569. Examples of dry binders include magnesium stearate, zinc stearate and magnesium myristate. Examples of absorbents include kaolin, spherical silicas such as MSS-500/3H, acrylates copolymer such as Polytrap and allyl methacrylates crosspolymers such as Polypore E200. Examples of astringents include witch hazel and alun. Sebum displacers include sodium C8–16 isoalkylsuccinyl wheat or soy protein. Examples of preservatives include methylparaben, germall 115, which is a blend of preservatives, propylparaben and imidazolidinyl urea. Examples anti-caking agents include Dry Flo AF, a modified corn starch available from National Starch. Examples of texturizers include lauroyl lysine, micas such as mica SXI-5 which is mica that is surface-modified with silica beads, mica 217N-I2 available from Kobo and which is mica that is surface modified with nylon, boron nitrides such as BN CC66058 available from Advanced Ceramics, and LBN-I2S which is an acrylates copolymer modified with boron nitride and isopropyl titanium triisostearate in accordance with U.S. Pat. No. 5,246,780 which is specifically incorporated by reference herein, crosspolymers such as Hexyldecyldiisocyanate/Trimethylol Hexylactone Crosspolymer, and acrylates copolymers.

The compositions of the present invention are preferably prepared according to the following general steps. Typically, a dry phase is prepared, a liquid phase is prepared and then the two phases are combined to provide the ultimate composition. The dry phase is made by adding all the dry ingredients to the container of a blender, for example a mason jar that is adapted for use with an Osterizer blender. The blade of the blender is attached to the jar, and the jar and blade are attached to the blender. The mixture of dry ingredients is blended for 3 minutes on the "liquefy" setting or preferably for the amount of time and strength of agitation to homogenize the ingredients.

If desired, the blended dry phase can be passed as needed, preferably once or twice, through a micropulverizer adapted with a screen, such as an 0.010" herringbone screen to achieve the desired consistency. The micropulverizer can be, for example, a sample mill or, preferably, a center-feed mill. A person of skill in the art will recognize when it would be advantageous to use an appropriate pulverizer after this or any subsequent blending step, for example to improve the consistency of the blended components. The skilled artisan will also be able to choose an appropriate screen for use with the pulverizer.

It is preferred to add certain liquid ingredients, such as astringents, to the dry phase. This is accomplished by making a powderized premix of the liquid components. The powderized premix is prepared by mixing the liquid components together with a solid carrier, such as calcium silicate, that is compatible with the dry phase. The premix is blended by handmixing the components of the premix. Especially in instances where the consistency is not very even or where the final composition develops a mottled appearance, the premix ingredients can be blended together in a blender and then passed through a micropulverizer adapted with an appropriately sized screen, for example an 0.010" herringbone screen.

The blended premix is then added to the other dry ingredients. Preferably, the premix is added to the mason jar containing the dry ingredients prior to homogenizing the dry ingredients. However, the premix could also be mixed by hand or by machine into the already homogenized dry ingredients.

The liquid phase is made by weighing the various liquid ingredients into a beaker and stirring the solution to homogeneity.

The liquid phase is then added to the dry phase dropwise with a pipette. It is preferable to pipette drops into different parts of the dry blend while simultaneously using mechanical agitation, preferably swirling the mason jar by hand, to help get the liquid phase into different parts of the dry blend. After all of the liquid phase is swirled into the dry phase, the blade of the blender is reattached to the mason jar and the jar and blade are reattached to the blender. The combination of liquid and dry phases are mixed at the liquefy setting for two one minute intervals. In between the intervals, the sides of the mason jar should be scraped.

The final composition can be passed through a micropulverizer adapted with a screen, such as an 0.020" herringbone screen, to achieve the desired consistency. Generally, two passes through the screen are preferred. A person of ordinary skill in the art will recognize whether use of a pulverizer is preferred and if it is preferred, the preferred size of the screen. For example, some compositions of the present invention may have an appearance that is mottled with white specs after blending. It is preferred, at least for aesthetic reasons, to pass such a composition through a pulverizer adapted with an appropriately sized screen in order to achieve a better appearance for the composition. In general, it may be preferred to use a pulverizer after any of the blending steps, for example after blending the premix or after blending the dry phase ingredients or after blending the liquid phase. Again, an ordinarily skilled artisan should recognize the appropriateness of this step and should be able to select the appropriate equipment.

Variations of the above general method are encompassed by the present invention and should be recognizable by one of skill in the art. For example, in some instances, the liquid phase will not be homogeneous. In such instances, each liquid ingredient should be added by pipette into the dry phase individually. As another example, when preparing the dry phase, it may be preferable to combine all the dry ingredients which are difficult to grind plus some talc separately from the remaining dry ingredients as a first dry mixture. Thus, it may be preferable to blend the premix, the pigments and a portion of the talc in a blender, pass this mixture through a screen to obtain the right consistency and then add this first dry mixture to the remaining dry ingredients. As an additional example, in instances where the liquid binder is not compatible with the farnesol, farnesyl acetate and/or panthenyl triacetate, the liquid binder can be added to the dry phase independently from, and either before or after, the other liquid ingredients.

Further, the typical procedure described above is suitable for small scale preparation. A typical scale-up procedure is as follows. The dry ingredients are blended in a KitchenAid mixer using a whisk attachment for two 10 minute intervals. Between intervals, the sides of the container are scraped. After blending, the mixture is passed two times through a micropulverizer having an 0.010" herringbone screen. The liquid ingredients are combined in a suitable container, such as a separatory funnel, for dripping the liquid ingredients into the dry ingredients under agitation (i.e. while the KitchenAid is mixing). The composition is mixed for two 10 minute intervals and the container is scraped between intervals. After mixing, the composition is passed two times through a micropulverizer having an 0.020" herringbone screen.

The pressed powder form is obtained by adding the composition to a pan. and pressing the composition into the pan under pressure. The amount of pressure required for satisfactory results will be readily understood by a person of skill in the art and depends on the shape of the pan, for example the amount of pressure depends on the depth and cross-section of the pan. However, the amount of pressure will preferably be from about 800 pounds per square inch ("psi") to about 1000 psi for a 1551 Acme pan.

The pressed composition can be passed through a micropulverizer adapted with an appropriately sized screen (e.g., an 0.013" screen) to attain the appropriate consistency.

The invention may be more fully understood by consideration of the following examples, which are intended to be purely exemplary of the invention. It is not intended that the present invention be limited to these examples. Any modifications of the present invention which come within the spirit and scope of the appended claims should be considered part of the invention.

COMPARATIVE EXAMPLE 1

The following ingredients were used to form a pressed powder composition.

| Ingredient | % by weight |
|---|---|
| Dry Phase | |
| talc | 37.41 |
| pigments | 8.09 |
| binders | 10.00 |
| absorbents | 8.00 |
| astringent | 1.00 |
| sebum displacer | 1.00 |
| calcium silicate | 3.00 |
| preservatives | 0.50 |
| starch (anti-cake component) | 3.00 |
| texturizers | 22.00 |
| Liquid Phase | |
| laureth-2-octanoate | 6.00 |

The astringent, sebum displacer and calcium silicate were dropped into a beaker and hand mixed in order to prepare a premix. Next, the remaining dry ingredients were measured into a mason jar adapted for use with an Osterizer blender. The premix was then combined with the other dry ingredients in the mason jar and the contents of the jar were blended for three minutes at the liquefy setting to achieve a homogeneous mixture.

The liquid phase was pipetted into the homogeneous dry phase. Simultaneously, the dry phase was swirled by hand to enable the liquid phase to be added to different locations in the dry phase. After the liquid phase was completely added to the dry phase, the mixture was blended for an additional one minute. The sides of the mason jar were then scraped and once again the mixture was blended for a minute.

The final composition was pressed at 1100 psi in an 853 pan.

COMPARATIVE EXAMPLE 2

A second comparative powder composition was prepared in accordance with comparative Example 1 except that the liquid phase was formed from the ingredients listed below, which were first combined in a beaker and mixed together by swirling the beaker by hand before being pipetted into the dry phase.

| Ingredients | % by weight |
|---|---|
| Liquid Phase | |
| dimethylolpropane tetraisostearate | 0.90 |
| Tridecyl Neopentanoate | 1.50 |
| Octyldodecyl Stearoyl Stearate | 3.60 |

EXAMPLE 3

The following ingredients were used to form a powder composition in accordance with the present invention.

| Ingredient | % by weight small-scale | 1 kg scale-up |
|---|---|---|
| Dry Phase | | |
| talc | 35.41 | 354.10 |
| pigments | 8.09 | 80.90 |
| binders | 10.00 | 100.00 |
| absorbents | 8.00 | 80.00 |
| astringent | 1.00 | 10.00 |
| sebum displacer | 1.00 | 10.00 |
| calcium silicate | 3.00 | 30.00 |
| preservatives | 0.50 | 5.00 |
| starch (anti-cake component) | 3.00 | 30.00 |
| texturizers | 22.00 | 220.00 |
| | | (actual yield: 821.06 or 89.25%) |
| Liquid Phase | | |
| dimethylolpropane tetraisostearate | 0.90 | 8.03 |
| Tridecyl Neopentanoate | 1.50 | 13.39 |
| Octyldodecyl Stearoyl Stearate | 3.60 | 32.13 |
| Unitrienol T-27 | 2.00 | 17.85 |

The small-scale sample was made in accordance with the procedures used for the second comparative powder composition. The 1 kg scale-up composition was made according to the following directions.

The astringent, sebum displacer and calcium silicate were dropped into a beaker and hand mixed in order to prepare a premix. Next, the remaining dry ingredients were measured into a mixing bowl adapted for use with a KitchenAid mixer fitted with a whisk attachment. The premix was then combined with the other dry ingredients in the mixing bowl and the contents of the bowl were blended in the KitchenAid mixture for two ten minute intervals. The sides of the mixing bowl were scraped between intervals. After blending, the mixture was passed two times through a micropulverizer having an 0.010" herringbone screen.

The liquid phase was placed in a separatory funnel and swirled by hand to mix. Next, the liquid phase was dripped out of the funnel and into the homogeneous dry phase. The dry phase was agitated during the combining step by using the KitchenAid mixer with the whisk attachment. After the liquid phase was completely added to the dry phase, the mixture was blended for an additional ten minutes. The sides of the mixing bowl were then scraped and once again the mixture was blended for ten minutes. After, the composition was passed two times through a micropulverizer having an 0.020" herringbone screen.

The composition was pressed at 1100 psi into an 853 pan.

It was observed that comparative Example 1 was slightly dusty and had less color development than comparative Example 2. Comparative Example 2 had more coverage, a nice even lay-down on the skin and finer texture relative to comparative Example 1. Example 3 had the best texture among the three compositions, being significantly more silky than comparative Example 2. Five cosmetic chemists who are not powder specialists also concluded that there was a difference in texture between the composition of Example 3 and the composition of comparative Example 2.

EXAMPLE 4

The following powder composition was prepared according to the present invention, in accordance with the procedure described for comparative Example 2, except that the composition was pressed at 1500 psi in a 1551 pan.

| Ingredient | % by weight |
|---|---|
| Dry Phase | |
| talc | 40.41 |
| pigments | 8.09 |
| binders | 5.00 |
| absorbents | 8.00 |
| astringent | 1.00 |
| sebum displacer | 1.00 |
| calcium silicate | 3.00 |
| preservatives | 0.50 |
| starch (anti-cake component) | 3.00 |
| texturizers | 22.00 |
| Liquid Phase | |
| trimethylpropane triisostearate | 0.90 |
| isocetyl stearoyl stearate | 2.25 |
| tridecyl neopentanoate | 1.50 |
| diisostearyl malate | 1.35 |
| Unitrienol T-27 | 2.00 |

EXAMPLE 5

Example 5 was prepared in accordance with Example 4, except that the liquid phase included different ingredients as listed below.

| Ingredient | % by weight |
|---|---|
| Liquid Phase | |
| diisostearyl malate | 0.90 |
| isocetyl stearoyl stearate | 1.50 |
| tridecyl neopentanoate | 1.80 |
| triisostearyl citrate | 1.80 |
| Unitrienol T-27 | 2.00 |

EXAMPLE 6

The following powder composition was prepared according to the present invention.

| Ingredient | % by weight |
|---|---|
| Dry Phase | |
| talc | 38.61 |
| pigments | 8.09 |
| binders | 5.00 |

-continued

| Ingredient | % by weight |
|---|---|
| absorbents | 7.50 |
| astringent | 1.00 |
| sebum displacer | 1.00 |
| silica | 2.00 |
| preservatives | 0.50 |
| starch (anti-cake component) | 3.00 |
| texturizers | 25.30 |
| Liquid Phase | |
| trimethylpropane triisostearate | 0.90 |
| isocetyl stearoyl stearate | 2.25 |
| tridecyl neopentanoate | 1.50 |
| diisostearyl malate | 1.35 |
| Unitrienol T-27 | 2.00 |

The small-scale sample was made in accordance with the general procedures described above. In particular, a premix was made from the astringent, sebum displacer and silica by blending the ingredients using a Baker Perkins mixer and then passing the blended components through a center-feed mill equipped with an 0.010" herringbone screen.

The pre-mix was added to the remaining dry ingredients. The dry ingredients were blended for three minutes in an Osterizer blender set at liquefy.

Next the liquid phase was swirled together by hand, in a beaker and pipetted into the dry ingredients. The combined liquid and dry phase were then blended together in an Osterizer blender set at liquefy for one minute. The blended ingredients were passed once through a center-feed mill equipped with an 0.020" herringbone screen.

The final composition was pressed at 1000 psi in a 1551 pan.

EXAMPLE 7

The following composition was prepared in accordance with the present invention.

| Ingredient | % by weight |
|---|---|
| Dry Phase | |
| talc | 35.61 |
| pigments | 8.09 |
| binders | 5.00 |
| absorbents | 7.50 |
| astringent | 1.00 |
| sebum displacer | 1.00 |
| silica | 2.00 |
| preservatives | 0.50 |
| starch (anti-cake component) | 3.00 |
| texturizers | 25.30 |
| Liquid Phase | |
| trimethylpropane triisostearate | 0.90 |
| isocetyl stearoyl stearate | 2.25 |
| tridecyl neopentanoate | 1.50 |
| diisostearyl malate | 1.35 |
| Unitrienol T-27 | 5.00 |

The composition of Example 7 was prepared using a similar procedure as that of Example 6 except that the dry phase was passed through a center-feed mill equipped with an 0.010" herringbone screen and the final composition was pressed at 800 psi in a 1551 pan.

EXAMPLE 8

Example 8 was prepared in accordance with the present invention following the procedures described in connection with Example 7.

| Ingredient | % by weight |
|---|---|
| Dry Phase | |
| talc | 38.61 |
| pigments | 8.09 |
| binders | 5.00 |
| absorbents | 7.50 |
| astringent | 1.00 |
| sebum displacer | 1.00 |
| silica | 2.00 |
| preservatives | 0.50 |
| starch (anti-cake component) | 3.00 |
| texturizers | 25.30 |
| Liquid Phase | |
| Unitrienol T-27 | 8.00 |

It was observed that the composition of Example 8 had a silky texture but was also very dusty and not as bound as compared to inventive powder compositions of Examples 6 and 7. Furthermore, the press was soft at all pressures.

EXAMPLE 9

| Ingredient | % by weight |
|---|---|
| Premix | |
| silica | 2.00 |
| astringent | 1.00 |
| sebum displacer | 1.00 |
| Color Concentrate | |
| talc | 12.00 |
| preservative | 0.20 |
| premix | 4.00 |
| pigments | 1.46 |
| Dry Phase | |
| talc | 24.24 |
| pigments | 6.00 |
| binders | 5.00 |
| absorbents | 7.50 |
| preservatives | 0.30 |
| starch (anti-cake component) | 3.00 |
| texturizers | 25.30 |
| Liquid Phase | |
| isocetyl stearoyl stearate | 3.15 |
| tridecyl neopentanoate | 1.50 |
| diisostearyl malate | 1.35 |
| Unitrienol T-27 | 5.00 |

EXAMPLES 10 AND 11

| | % by weight | |
|---|---|---|
| Ingredient | Example 10 | Example 11 |
| Premix | | |
| astringent | 1.00 | 1.00 |
| sebum displacer | 1.00 | 1.00 |
| silica | 2.00 | 2.00 |
| Dry Phase | | |
| talc | 35.61 | 35.924 |
| pigments | 8.09 | 7.776 |

-continued

| | % by weight | |
|---|---|---|
| Ingredient | Example 10 | Example 11 |
| binders | 5.00 | 5.00 |
| absorbents | 7.50 | 7.50 |
| preservatives | 0.50 | 0.50 |
| starch(anti-cake component) | 3.00 | 3.00 |
| texturizers | 25.30 | 25.30 |
| Liquid Phase | | |
| trimethylpropane triisostearate | 0.90 | 0.90 |
| isocetyl stearoyl stearate | 2.25 | 2.25 |
| tridecyl neopentanoate | 1.50 | 1.50 |
| diisostearyl malate | 1.35 | 1.35 |
| Unitrienol T-27 | 5.00 | 5.00 |

A premix was prepared by blending the silica, sebum displacer and astringent together in a Baker Perkins mixer and then passing the blended components one time through a center-feed mill equipped with an 0.010" herringbone screen.

The dry ingredients, including the premix were then placed in a bowl of a KitchenAid mixer and blended together for two ten minute intervals. In between the blending intervals, the sides of the mixing bowl were scraped. The blended dry phase composition was then passed twice through a micropulverizer equipped with an 0.010" herringbone screen.

The liquid ingredients were combined and swirled together in a separatory funnel. The blended liquid components were then dripped into the dry phase, under agitation. The mixture was blended for two ten minute intervals using the KitchenAid mixer. Between intervals, the sides of the mixing bowl were scraped.

After blending, the composition was passed two times through a micropulverizer equipped with an 0.013" herringbone screen.

Lab samples were pressed at 800 psi in a 1551 pan and were observed to be smooth and creamy under the fingers. Samples applied to the skin appeared natural and not dry or matte looking.

Scale-up samples were pressed at 1500 psi in a 1551 pan. The texture of the composition of these samples was observed to be fine, light and weightless. Furthermore, the composition felt very natural and wore well on the skin.

COMPARATIVE EXAMPLES 12–14 AND EXAMPLE 15

| | % by weight | | | |
|---|---|---|---|---|
| Ingredient | Example 12 | Example 13 | Example 14 | Example 15 |
| Dry Phase | | | | |
| talc | 87.91 | 82.91 | 82.91 | 82.91 |
| binders | 3.50 | 3.50 | 3.50 | 3.50 |
| preservatives | 0.50 | 0.50 | 0.50 | 0.50 |
| pigments | 2.09 | 2.09 | 2.09 | 2.09 |
| Liquid Phase | | | | |
| octyl palmitate | 6.00 | 6.00 | 6.00 | 6.00 |
| farnesol (Dragoco) | | 5.00 | | |

-continued

| | % by weight | | | |
|---|---|---|---|---|
| Ingredient | Example 12 | Example 13 | Example 14 | Example 15 |
| D-Panthenyl Triacetate (Lipo) | | | 5.00 | |
| Unitrienol T-27 | | | | 5.00 |

The dry phase ingredients were added to a mason jar and blended together for three minutes using an Osterizer blender on the liquefy setting. The liquid phase ingredients were placed in a beaker, and where appropriate, swirled together to blend the ingredients. The liquid phase ingredients were then pipetted into the dry phase ingredients and mixed together for one minute in the Osterizer blender. The sides of the jar holding the ingredients were scraped and the components were once again blended together in the Osterizer for one minute. The composition was then pressed using a Kemwall handpress into a 1551 pan.

It was observed that the Unitrienol T-27 and the farnesol were compatible with the octyl palmitate but that the panthenyl triacetate was not, even after application of heat and extended mixing. It was also observed that the composition of comparative Example 14 had a less desirable texture than that of comparative Example 12; the texture was heavy, slightly gritty and not as fine as the texture of comparative Example 12.

The texture of comparative Example 13 under the fingers was observed to be similar to that of comparative Example 12, superior to that of comparative Example 14 but inferior to the composition of Example 15.

The texture under the fingers of the composition of Example 15 was observed to be the best among samples 12–15.

COMPARATIVE EXAMPLE 16 AND EXAMPLES 17–18

| | % by weight | | |
|---|---|---|---|
| Ingredient | Example 16 | Example 17 | Example 18 |
| Dry Phase | | | |
| talc | 82.91 | 86.91 | 84.91 |
| binders | 3.50 | 3.50 | 3.50 |
| preservatives | 0.50 | 0.50 | 0.50 |
| pigments | 2.09 | 2.09 | 2.09 |
| Liquid Phase | | | |
| octyl palmitate | 6.00 | 6.00 | 6.00 |
| farnesol | 2.50 | | |
| Panthenyl Triacetate | 2.50 | | |
| Unitrienol T-27 | | 1.00 | 3.00 |

The compositions of comparative Example 16 and Examples 17 an 18 were made in accordance with the procedure described above, in connection with comparative Examples 12–14 and Example 15.

It was observed that the composition of comparative Example 16 was superior in feel to comparative Example 14.

It was further observed that the cake tone of the composition of comparative Example 16 was less intense/lighter in color than the cake tone of both the composition of comparative Example 13 and the composition of Example 15. Further, as compared to the composition of Example 13, the texture of comparative Example 16 is less draggy and has a more creamy texture.

It was further observed that the composition of comparative Example 16 was slightly more heavy, oily and draggy feeling than the composition of Example 15 which was lighter and drier feeling as well as more silky, and exhibiting more slip and less drag. Finally, it was observed that all samples containing Unitrienol (i.e. samples 15, 17 and 18) were superior in texture to those without Unitrienol T-27 (i.e. samples 12–14 and 16) as determined by a blind sensory test.

EXAMPLES 19–22 AND COMPARATIVE EXAMPLE 23

| Ingredient | % by weight | | | | |
| --- | --- | --- | --- | --- | --- |
|  | Ex.19 | Ex.20 | Ex.21 | Ex.22 | Ex.23 |
| Dry Phase | | | | | |
| talc | 86.91 | 90.91 | 91.41 | 91.66 | 91.91 |
| binders | 3.50 | 3.50 | 3.50 | 3.50 | 3.50 |
| preservatives | 0.50 | 0.50 | 0.50 | 0.50 | 0.50 |
| pigments | 2.09 | 2.09 | 2.09 | 2.09 | 2.09 |
| Liquid Phase | | | | | |
| octyl palmitate | 2.00 | 2.00 | 2.00 | 2.00 | 2.00 |
| Unitrienol T-27 | 5.00 | 1.00 | 0.50 | 0.25 | 0.00 |

The compositions of Examples 19–22 and comparative Example 23 were made in accordance with the procedure described in connection with comparative Examples 12–14 and Example 15.

Sensory tests indicated that the presence of Unitrienol T-27 was detectable in all the samples 19–22 when compared with comparative sample 23 due to differences in texture.

In particular, the composition of Example 19 was texturally superior, feeling lighter and silkier under the finger and having a more natural looking coverage/appearance relative to the composition of comparative Example 23.

The composition of Example 20 was also texturally superior to that of comparative Example 23. The composition of Example 20 felt lighter and silkier under the fingers than the composition of comparative Example 23, and also the coverage and appearance of sample 20 was better than that of comparative sample 23. However, sample 20 was slightly less light and silky than sample 19.

The compositions of Examples 21 and 22 were also observed to be texturally different than the composition of comparative Example 23; samples 21 and 22 were picked out of a line-up as being texturally different than sample 23 using a tactile evaluation.

EXAMPLES 24–25 AND COMPARATIVE EXAMPLES 26–27

| Ingredient | % by weight | | | |
| --- | --- | --- | --- | --- |
|  | Ex.24 | Ex.25 | Ex.26 | Ex.27 |
| Dry Phase | | | | |
| talc | 93.91 | 93.91 | 95.91 | 95.91 |
| pigments | 2.09 | 2.09 | 2.09 | 2.09 |
| Liquid Phase | | | | |
| dimethicone | 1.62 | 1.442 | 1.442 | 1.62 |
| cetyl dimethicone | 0.25 | 0.20 | 0.20 | 0.25 |
| dimethiconol |  | 0.185 | 0.185 |  |
| triisocetyl citrate |  | 0.10 | 0.10 |  |
| trimethylsiloxysilicate | 0.13 | 0.053 | 0.053 | 0.13 |
| cyclopentasiloxane |  | 0.02 | 0.02 |  |
| Unitrienol T-27 | 2.00 | 2.00 |  |  |

The compositions of Examples 24 and 25 and comparative Examples 26 and 27 were prepared by first mixing the dry phase ingredients for three minutes in an Osterizer 10-speed blender. The silicone liquid binder components were premixed and added to the dry phase separately from the Unitrienol T-27. The combination of liquid and dry ingredients was blended together for one minute in the Osterizer blender. The sides of the jar were scraped and the mixture was once again blended for one minute. A pressed powder was prepared by pressing the composition at 250 psi into a 1551 pan.

Comparative samples 26 and 27 (without Unitrienol T-27) were observed to be less creamy on the surface of the cake than the composition of Example 19. On the skin, sample 25 was observed to be less white (indicated better pigment wetting) and more natural looking than comparative sample 26. Further, sample 25 had better skin adhesion than comparative sample 26. Finally, it was also observed that sample 24 was less white and had slightly better skin adhesion and better color development than comparative sample 27.

EXAMPLE 28

| Ingredient | % by weight |
| --- | --- |
| Dry Phase | |
| talc | 36.249 |
| pigments | 7.451 |
| binders | 5.00 |
| absorbents | 7.50 |
| astringent | 1.00 |
| sebum displacer | 1.00 |
| silica | 2.00 |
| preservatives | 0.50 |
| starch (anti-cake component) | 3.00 |
| texturizers | 25.30 |
| Liquid Phase | |
| isostearyl neopentanoate | 1.50 |
| isocetyl stearoyl stearate | 3.14 |
| diisostearyl malate | 1.36 |
| Unitrienol T-27 | 5.00 |

Composition 28 was prepared by first blending the dry ingredients in a 10 liter Baker Perkins at 500 rpm using the bottom blade only for two ten minute intervals. The bowl was scraped in between the intervals. After blending, the mixture was passed through a pulverizer fitted with an 0.010" herringbone screen.

The liquid phase was combined in a separatory funnel and then dripped into the dry phase under agitation. Once the liquid phase was added, the mixture was blended at 250 rpm using only the bottom blade for ten minutes. The sides of the bowl were scraped and the mixture was again blended for ten minutes at 250 rpm using only the bottom blade. The resulting mixture was passed two times through a pulverizer fitted with an 0.013" herringbone screen.

The texture of sample 28 was observed to be very similar to the composition of Example 10, having a great feel under the fingers.

COMPARATIVE EXAMPLE 29

| Ingredient | % by weight |
| --- | --- |
| Dry Phase | |
| talc | 82.91 |
| pigments | 2.09 |
| binders | 3.50 |
| preservatives | 0.50 |
| Liquid Phase | |
| octyl palmitate | 6.00 |
| farnesyl acetate | 5.00 |

The composition of comparative Example 29 was made according to the procedure described in connection with comparative Examples 12–14 and Example 15 above.

It was observed that the composition of comparative Example 29 was texturally inferior to the composition of Example 15 but superior to comparative Examples 13 and 14.

COMPARATIVE EXAMPLE 30

The ingredients listing on the Estee Lauder Double Matte Pressed Powder package indicates that the following components are present in the Lauder product, presumably in order of largest to smallest amount: Talc; C12–15 Alkyl Octanoate; Zinc Stearate; C9–15 Fluoroalcohol; Perfluoroalkyl Phosphate; Lauryl Lysine; Panthenyl Triacetate; Pentaerythrityl Tetraoctanoate; Farnesyl Acetate; Acrylates Copolymer; Bisabolol; Polyperfluoroisopropyl Ether; Methylpolysilsesquioxane; Farnesol; Sodium Hyaluronate; BHT; Phenoxyethanol; Isopropylparaben; Isobutylparaben; Butylparaben. The listing also indicates that the product may contain: Mica, Titanium Dioxide and Iron Oxides.

Although the Lauder product reportedly contains panthenyl triacetate, farnesyl acetate and farnesol, the Lauder product did not have all the beneficial characteristics of certain compositions described above of the present invention. In particular, the compositions of the present invention have an improved texture over and feel silkier than the Lauder product. Furthermore, the Lauder product was found unacceptable for most aspects. The Lauder powder was observed to glaze very easily, shift in color when the skin is oily and become cakey after several hours wear.

Interestingly, although the ingredients list on the package of the Lauder product indicates that panthenyl triacetate should be present in the composition to a significant extent (since it is high on the list of ingredients), as illustrated in FIGS. 1–9, chromatographic analysis of the Estee Lauder product indicates the possibility that panthenyl triacetate is absent or present only in trace amounts in the Lauder product.

Figure 2:
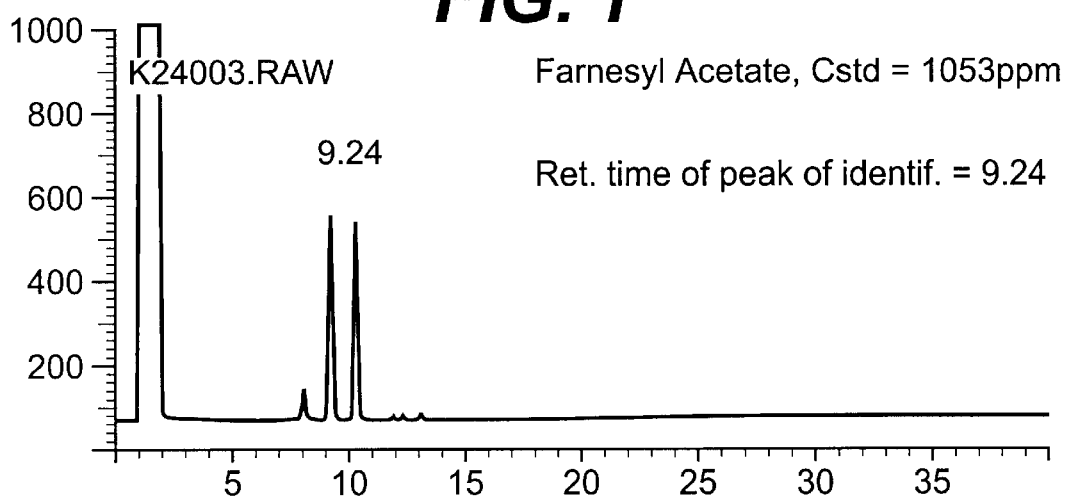
FIG. 2 is a chromatogram of a sample of farnesyl acetate.
Figure 3:
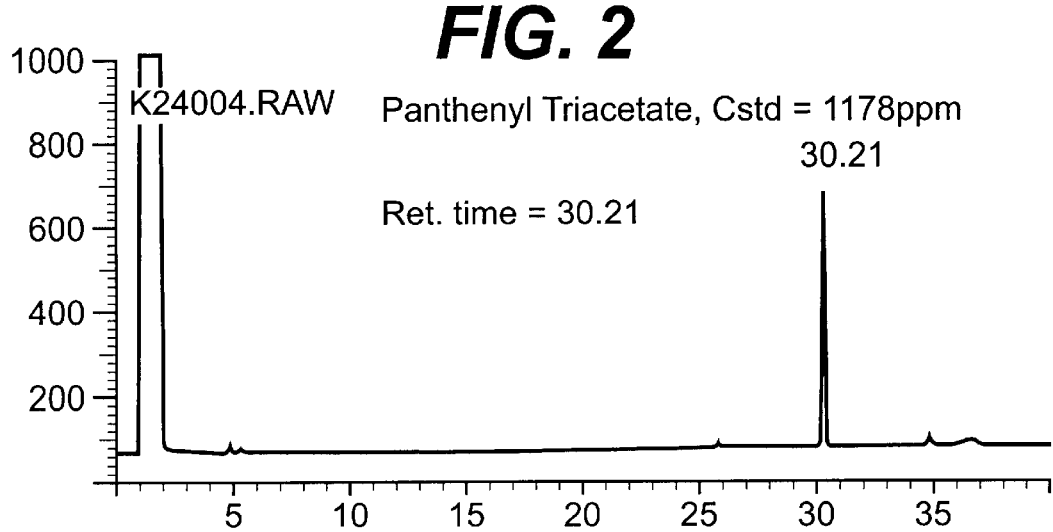
FIG. 3 is a chromatogram of a sample of panthenyl triacetate.
Figure 4:
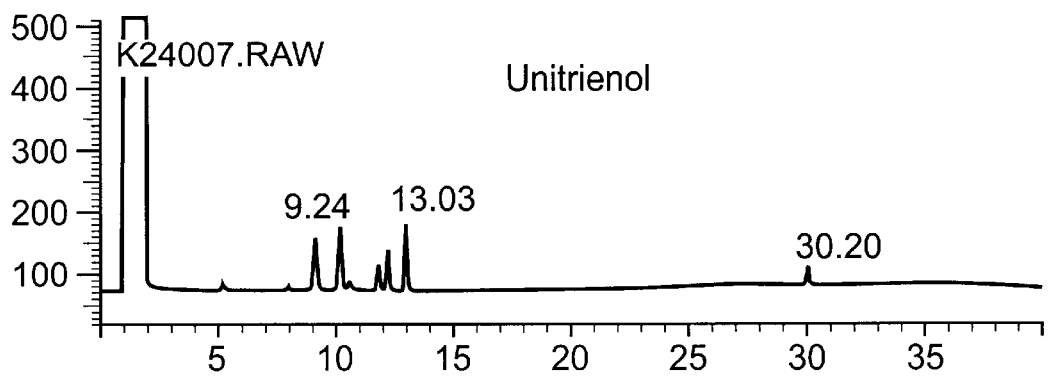
FIG. 4 is a chromatogram of a sample of Unitrienol T-27.
Figure 5:
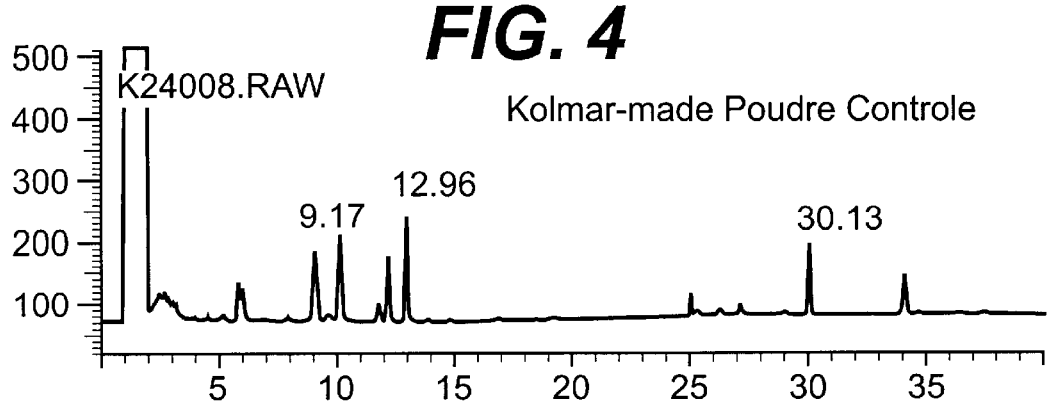
FIG. 5 is a chromatogram of a sample of a composition in accordance with the present invention.
Figure 6:
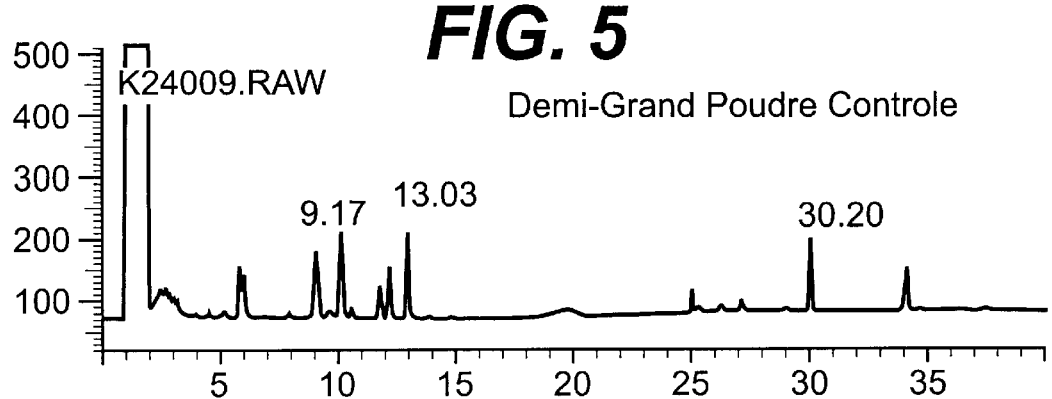
FIG. 6 is a chromatogram of a sample of another composition in accordance with the present invention.
Figure 7:
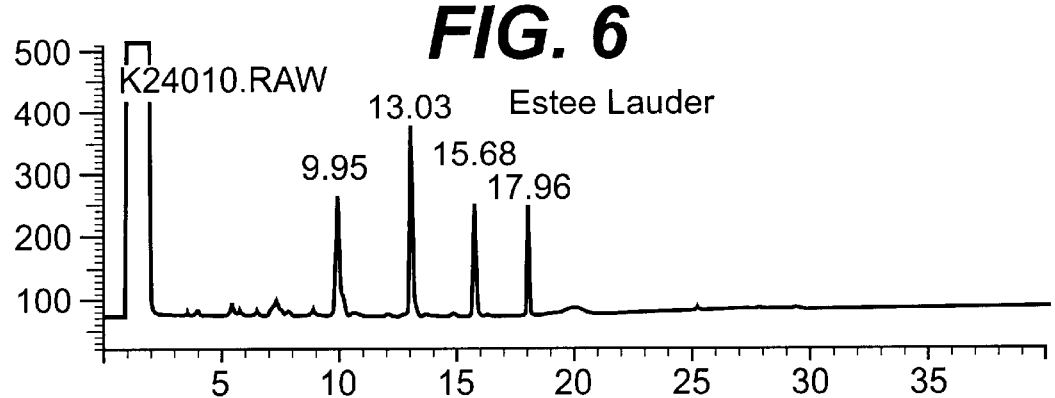
FIG. 7 is a chromatogram of a sample of Estee Lauder Double Matte Pressed Powder.

Referring now to the figures, FIG. 1, a gas chromatogram of farnesol, indicates that compositions containing farnesol should show a peak in the chromatogram at about 13.06. FIG. 2, a gas chromatogram of farnesyl acetate, indicates that compositions containing this compound should have a peak at about 9.24. Finally, FIG. 3, a gas chromatogram of panthenyl triacetate, indicates that compositions containing this ingredient should have a peak at about 30.21. As expected, the gas chromatogram of Unitrienol T-27, FIG. 4, has peaks at 9.24, 13.03 and 30.20. Similarly, as illustrated in FIGS. 5 and 6, compositions prepared in accordance with the present invention showed the expected peaks (at 9.17, 12.96 and 30.13 for one composition and 9.17, 13.03 and 30.20 for another composition). However, as illustrated in FIG. 7, the expected peak at 30.21 for panthenyl triacetate was absent in the Estee Lauder product.

Figure 8:
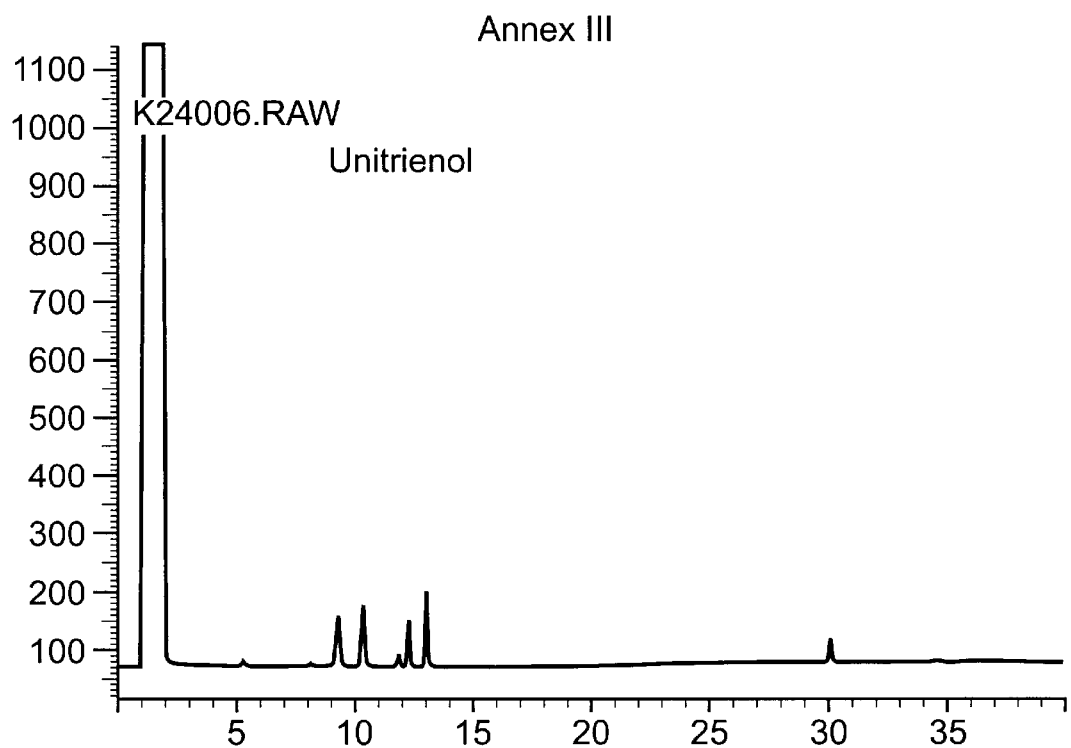
FIG. 8 is a another chromatogram of a sample of Unitrienol T-27.
Figure 9:
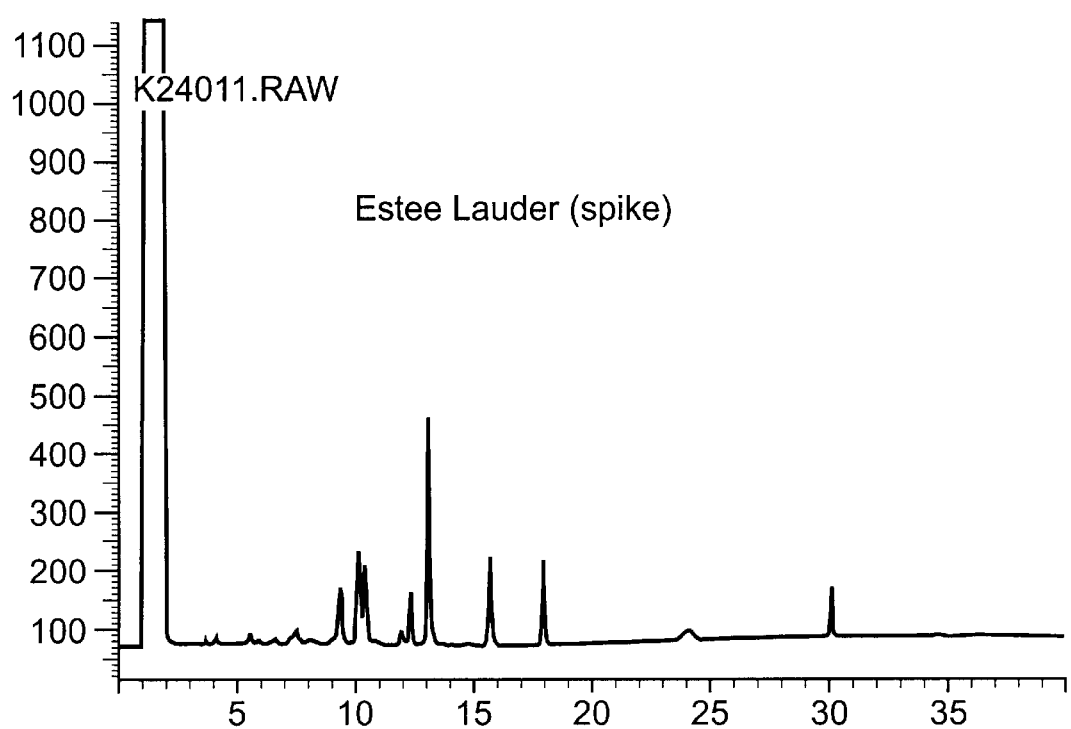
FIG. 9 is a chromotagram of a sample of Estee Lauder Double Matte Pressed Powder spiked with a sample of Unitrienol T-27.

FIGS. 8 and 9 are chromatograms of a sample of Unitrienol T-27 and the Estee Lauder product spiked with the same sample of Unitrienol T-27. As expected, the spiked Estee Lauder product demonstrated all three peaks. Interestingly, the height of the panthenyl triacetate peak was greater than expected from the results illustrated in FIG. 8. The reason for this phenomenon is unknown.

It should be understood that the specifically disclosed embodiments are exemplary in nature and not intended to be construed as limiting the scope of the invention, as set forth in the claims. For example, the amounts of ingredients described in each embodiment can be adjusted according to the specific features of the cosmetic composition into which the panthenyl triacetate, farnesol and farnesyl acetate is incorporated by those skilled in the cosmetic composition, art. The scope of the invention is intended to cover such alternatives and modifications and equivalents as may be included within the spirit and scope of the appended claims.

What is claimed is:

1. A cosmetic powder composition comprising farnesol, farnesyl acetate and panthenyl triacetate wherein said farnesol, said farnesyl acetate and said panthenyl triacetate are present in said composition in an amount effective for improving texture.

2. The powder composition of claim 1 further comprising a liquid binder system comprising at least one liquid binder.

3. The powder composition of claim 2 wherein said farnesol, farnesyl acetate and panthenyl triacetate are present in said composition in a total amount ranging from 0.20% to 9% by weight of the total composition and said liquid binder system is present in said composition in an amount ranging from 0.4% to 11% by weight of the total composition.

4. The powder composition of claim 3 wherein said farnesol, farnesyl acetate and panthenyl triacetate are present in said composition in a total amount ranging from 0.25% to 8% by weight of the total composition and said liquid binder system is present in said composition in an amount ranging from 0.5% to 10% by weight of the total composition.

5. The powder composition of claim 3 wherein said farnesol, farnesyl acetate and panthenyl triacetate are present in said composition in a total amount ranging from 1% to 5% by weight of the total composition.

6. The powder composition of claim 3 wherein said composition further comprises at least one pigment.

7. The powder composition of claim 5 wherein said liquid binder system comprises at least one compound chosen from tridecyl neopentanoate, octyl palmitate, isocetyl stearoyl stearate, octyldodecyl stearoyl stearate, laureth-2-octanoate, dimethylolpropane tetraisostearate, isocetyl stearyl stearate, diisostearyl malate, triisostearyl citrate, trimethylpropane triisostearate, dimethicone, cetyl dimethicone, dimethiconol, triisocetyl citrate, trimethylsiloxysilicate, cyclopentasiloxane, triisostearyl citrate and isostearyl neopentanoate.

8. The powder composition of claim 7 wherein said at least one pigment is a mixture of pigments.

9. The powder composition of claim 6 wherein said at least one pigment is present in said composition in an amount of up to 90% by weight.

10. The powder composition of claim 6 wherein said at least one pigment is present in said composition in an amount of from 1% to 10% by weight of the total composition.

11. The powder composition of claim 6 wherein said powder composition is a pressed powder.

12. The powder composition of claim 6 wherein said composition further comprises at least one binder, at least one absorbent, at least one astringent, at least one preservative and at least one anti-cake component.

13. A cosmetic powder composition comprising farnesol, farnesyl acetate and panthenyl triacetate wherein said farnesol, said farnesyl acetate and said panthenyl triacetate comprise a liquid blend.

14. The powder composition of claim 13 wherein said liquid blend is Unitrienol T-27.

15. The powder composition of claim 13 wherein said farnesol, farnesyl acetate and said panthenyl triacetate are present in said blend and provided in said composition in amounts effective for improving texture.

16. The powder composition of claim 14 wherein said Unitrienol T-27 is present in said composition in an amount effective for improving texture.

17. The powder composition of claim 15 wherein each of said farnesol, farnesyl acetate and panthenyl triacetate are present in said liquid blend in an amount ranging from 15% to 65% by weight of said blend.

18. The powder composition of claim 17 wherein each of said farnesol, farnesyl acetate and panthenyl triacetate are present in said liquid blend in an amount ranging from 25% to 50% by weight of said blend.

19. The powder composition of claim 15 further comprising a liquid binder system comprising at least one liquid binder.

20. The powder composition of claim 19 wherein said farnesol, farnesyl acetate and panthenyl triacetate are present in said composition in a total amount ranging from 0.20% to 9% by weight of the total composition and said liquid binder system is present in said composition in an amount ranging from 0.4% to 11% by weight of the total composition.

21. The powder composition of claim 20 wherein said farnesol, farnesyl acetate and panthenyl triacetate are present in said composition in a total amount ranging from 0.25% to 8% by weight of the total composition and said liquid binder system is present in said composition in an amount ranging from 0.5% to 10% by weight of the total composition.

22. The powder composition of claim 20 wherein said farnesol, farnesyl acetate and panthenyl triacetate are present in said composition in a total amount ranging from 1% to 5% by weight of the total composition.

23. The powder composition of claim 20 wherein said composition further comprises at least one pigment.

24. The powder composition of claim 19 wherein said liquid binder system comprises at least one compound selected from tridecyl neopentanoate, octyl palmitate, isocetyl stearoyl stearate, octyldodecyl stearoyl stearate, laureth-2-octanoate, dimethylolpropane tetraisostearate, isocetyl stearyl stearate, diisostearyl malate, triisostearyl citrate, trimethylpropane triisostearate, dimethicone, cetyl dimethicone, dimethiconol, triisocetyl citrate, trimethylsiloxysilicate, cyclopentasiloxane, triisostearyl citrate and isostearyl neopentanoate.

25. The powder composition of claim 24 wherein said at least one pigment is a mixture of pigments.

26. The powder composition of claim 23 wherein said at least one pigment is present in said composition in an amount up to 90% by weight.

27. The powder composition of claim 26 wherein said at least one pigment is present in said composition in an amount of from 1% to 10% by weight of the total composition.

28. The powder composition of claim 23 wherein said powder composition is a pressed powder.

29. The powder composition of claim 23 wherein said composition further comprises at least one binder, at least one absorbent, at least one astringent, at least one preservative and at least one anti-cake component.

30. The powder composition of claim 16 further comprising a liquid binder system comprising at least one liquid binder.

31. The powder composition of claim 30 wherein said Unitrienol T-27 is present in said composition in an amount ranging from 0.20% to 9% by weight of the total composition and said liquid binder system is present in said composition in an amount ranging from 0.4% to 11% by weight of the total composition.

32. The powder composition of claim 31 wherein said Unitrienol T-27 is present in said composition in an amount ranging from 0.25% to 8% by weight of the total composition and said liquid binder system is present in said composition in an amount ranging from 0.5% to 10% by weight of the total composition.

33. The powder composition of claim 31 wherein said Unitrienol T-27 is present in said composition in an amount ranging from 1% to 5% by weight of the total composition.

34. The powder composition of claim 31 wherein said composition further comprises at least one pigment.

35. The powder composition of claim 30 wherein said liquid binder system comprises at least one compound chosen from tridecyl neopentanoate, octyl palmitate, isocetyl stearoyl stearate, octyldodecyl stearoyl stearate, laureth-2-octanoate, dimethylolpropane tetraisostearate, isocetyl stearyl stearate, diisostearyl malate, triisostearyl citrate, trimethylpropane triisostearate, dimethicone, cetyl dimethicone, dimethiconol, triisocetyl citrate, trimethylsiloxysilicate, cyclopentasiloxane, triisostearyl citrate and isostearyl neopentanoate.

36. The powder composition of claim 35 wherein said at least one pigment is a mixture of pigments.

37. The powder composition of claim 34 wherein said at least one pigment is present in said composition in an amount up to 90% by weight.

38. The powder composition of claim 37 wherein said at least one pigment is present in said composition in an amount of from 1% to 10% by weight of the total composition.

39. The powder composition of claim 34 wherein said powder composition is a pressed powder.

40. The powder composition of claim 34 wherein said composition further comprises at least one binder, at least one absorbent, at least one astringent, at least one preservative and at least one anti-cake component.

41. A method for improving the texture of a cosmetic composition comprising including an effective amount of farnesol, farnesyl acetate and panthenyl triacetate in said composition.

42. A method for improving the texture of a cosmetic composition comprising including an effective amount of a blend of farnesol, farnesyl acetate and panthenyl triacetate in said composition.

43. The method for improving the texture of a cosmetic composition of claim 42 wherein said blend is Unitrienol T-27.

44. The method for improving the texture of a cosmetic composition of claim 42 wherein said farnesol, farnesyl acetate and panthenyl triacetate are each present in said blend in an amount ranging from 15% to 65% by weight of the blend.

45. The method for improving the texture of a cosmetic composition of claim 44 wherein said farnesol, farnesyl acetate and panthenyl triacetate are each present in said blend in an amount ranging from 25% to 50% by weight.

46. The method for improving the texture of a cosmetic composition of claim 41 further comprising including a liquid binder system comprising at least one liquid binder.

47. The method for improving the texture of a cosmetic composition of claim 46 wherein said farnesol, farnesyl acetate and panthenyl triacetate are present in said composition in an amount ranging from 0.20% to 9% by weight of the total composition and said liquid binder system is present in said composition in an amount ranging from 0.4% to 11% by weight of the total composition.

48. The method for improving the texture of a cosmetic composition of claim 47 wherein said farnesol, farnesyl acetate and panthenyl triacetate are present in said composition in an amount ranging from 0.25% to 8% by weight of the total composition and said liquid binder system is present in said composition in an amount ranging from 0.5% to 10% by weight of the total composition.

49. The method for improving the texture of a cosmetic composition of claim 47 wherein said farnesol, farnesyl acetate and panthenyl triacetate are present in said composition in a total amount ranging from 1% to 5% by weight of the total composition.

50. The method for improving the texture of a cosmetic composition of claim 47 further comprising including at least one pigment in said composition.

51. The method for improving the texture of a cosmetic composition of claim 50 wherein said liquid binder system comprises a compound chosen from tridecyl neopentanoate, octyl palmitate, isocetyl stearoyl stearate, octyldodecyl stearoyl stearate, laureth-2-octanoate, dimethylolpropane tetraisostearate, isocetyl stearyl stearate, diisostearyl malate, triisostearyl citrate, trimethylpropane triisostearate, dimethicone, cetyl dimethicone, dimethiconol, triisocetyl citrate, trimethylsiloxysilicate, cyclopentasiloxane, triisostearyl citrate and isostearyl neopentanoate.

52. The method for improving the texture of a cosmetic composition of claim 51 wherein said at least one pigment is a mixture of pigments.

53. The method of improving texture of a cosmetic composition of claim 51 wherein said at least one pigment is present in said composition in an amount ranging up to 90% by weight of the total composition.

54. The method of improving texture of a cosmetic composition of claim 53 wherein said at least one pigment is present in said composition in an amount ranging from 1% to 10% by weight of the total composition.

55. The method of improving texture of a cosmetic composition of claim 50 wherein said composition is a pressed powder composition.

56. The method of improving texture of a cosmetic composition of claim 50 further comprising including at least one binder, at least one absorbent, at least one astringent, at least one preservative and at least one anti-cake component.

57. The method for improving texture of a cosmetic composition of claim 42 further comprising including a liquid binder system comprising at least one liquid binder.

58. The method for improving texture of a cosmetic composition of claim 57 wherein said farnesol, farnesyl acetate and panthenyl triacetate are present in said composition in an amount ranging from 0.20% to 9% by weight of the total composition and said liquid binder system is present in said composition in an amount ranging from 0.4% to 11% by weight of the total composition.

59. The method for improving texture of a cosmetic composition of claim 58 wherein said farnesol, farnesyl acetate and panthenyl triacetate are present in said composition in an amount ranging from 0.25% to 8% by weight of the total composition and said liquid binder system is present in said composition in an amount ranging from 0.5% to 10% by weight of the total composition.

60. The method for improving texture of a cosmetic composition of claim 58 wherein said farnesol, farnesyl acetate and panthenyl triacetate are present in said composition in a total amount ranging from 1% to 5% by weight of the total composition.

61. The method for improving texture of a cosmetic composition of claim 58 further comprising including at least one pigment in said composition.

62. The method for improving texture of a cosmetic composition of claim 61 wherein said liquid binder system comprises a compound chosen from tridecyl neopentanoate, octyl palmitate, isocetyl stearoyl stearate, octyldodecyl stearoyl stearate, laureth-2-octanoate, dimethylolpropane tetraisostearate, isocetyl stearyl stearate, diisostearyl malate, triisostearyl citrate, trimethylpropane triisostearate, dimethicone, cetyl dimethicone, dimethiconol, triisocetyl citrate, trimethylsiloxysilicate, cyclopentasiloxane, triisostearyl citrate and isostearyl neopentanoate.

63. The method for improving texture of a cosmetic composition of claim 62 wherein said at least one pigment is a mixture of pigments.

64. The method of improving texture of a cosmetic composition of claim 62 wherein said at least one pigment is present in said composition in an amount ranging up to 10% by weight of the total composition.

65. The method of improving texture of a cosmetic composition of claim 64 wherein said at least one pigment is present in said composition in an amount ranging from 1% to 10% by weight of the total composition.

66. The method of improving texture of a cosmetic composition of claim 61 wherein said composition is a pressed powder composition.

67. The method of improving texture of a cosmetic composition of claim 61 further comprising including at least one binder, at least one absorbent, at least one astringent, at least one preservative and at least one anti-cake component.

* * * * *